United States Patent
Du et al.

(10) Patent No.: US 9,700,068 B2
(45) Date of Patent: Jul. 11, 2017

(54) FORMULATION OF COMPLEX CARBOHYDRATE FOR FODDER

(71) Applicant: Institute of Process Engineering, Chinese Academy of Sciences, Beijing (CN)

(72) Inventors: Yuguang Du, Beijing (CN); Qingsong Xu, Beijing (CN); Bo Shi, Beijing (CN); Qishun Liu, Beijing (CN); Gong Cheng, Beijing (CN)

(73) Assignee: INSTITUTE OF PROCESS ENGINEERING, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 15/036,009

(22) PCT Filed: Nov. 19, 2013

(86) PCT No.: PCT/CN2013/087425
§ 371 (c)(1),
(2) Date: Jun. 27, 2016

(87) PCT Pub. No.: WO2015/070470
PCT Pub. Date: May 21, 2015

(65) Prior Publication Data
US 2016/0295885 A1    Oct. 13, 2016

(30) Foreign Application Priority Data
Nov. 15, 2013 (CN) .......................... 2013 1 0575264

(51) Int. Cl.
| | | |
|---|---|---|
| *A61K 36/00* | (2006.01) | |
| *A23K 50/30* | (2016.01) | |
| *A23K 10/22* | (2016.01) | |
| *A23K 10/30* | (2016.01) | |
| *A23K 10/37* | (2016.01) | |
| *A23K 20/147* | (2016.01) | |
| *A23K 20/163* | (2016.01) | |
| *A23K 20/10* | (2016.01) | |
| *A23K 50/60* | (2016.01) | |
| *A61K 9/00* | (2006.01) | |
| *A61K 31/7004* | (2006.01) | |
| *A61K 31/7008* | (2006.01) | |
| *A61K 31/7012* | (2006.01) | |
| *A61K 35/60* | (2006.01) | |
| *A61K 36/48* | (2006.01) | |
| *A61K 36/899* | (2006.01) | |

(52) U.S. Cl.
CPC .............. *A23K 50/30* (2016.05); *A23K 10/22* (2016.05); *A23K 10/30* (2016.05); *A23K 10/37* (2016.05); *A23K 20/10* (2016.05); *A23K 20/147* (2016.05); *A23K 20/163* (2016.05); *A23K 50/60* (2016.05); *A61K 9/0056* (2013.01); *A61K 31/7004* (2013.01); *A61K 31/7008* (2013.01); *A61K 31/7012* (2013.01); *A61K 35/60* (2013.01); *A61K 36/48* (2013.01); *A61K 36/899* (2013.01); *Y02P 60/877* (2015.11)

(58) Field of Classification Search
None
See application file for complete search history.

(56) References Cited

FOREIGN PATENT DOCUMENTS

| CN | 102406069 A | 4/2012 |
|---|---|---|
| CN | 102919570 A | 2/2013 |

*Primary Examiner* — Qiuwen Mi
(74) *Attorney, Agent, or Firm* — Knobbe, Martens, Olson & Bear, LLP

(57) ABSTRACT

A formulation of complex carbohydrates for fodder, fodder comprising the same, and application, the fodder comprising of the following ingredients: corn, bean pulp, whey powder, fish meal, soymilk, wheat middling, piglet premix, glucose and a formulation of complex carbohydrates, and the formulation of complex carbohydrates consisting of flucose, galactose, N-acetylgalactosamine, glucosamine, acetylglucosamine, glucuronic acid, mannose, sialic acid and xylose.

9 Claims, No Drawings

FORMULATION OF COMPLEX CARBOHYDRATE FOR FODDER

FIELD OF THE INVENTION

The present invention belongs to the field of animal husbandry, more exactly, the present invention relates to a formulation of complex carbohydrates for fodder, fodder comprising same, and application.

BACKGROUND OF THE INVENTION

In recent years, the research of fodder additives is moving towards the direction of non-residue, non-drug resistance and improvement of human health and the environment. Weaned piglets can only rely on fodder to meet nutritional needs, and their digestive and immune system is not fully developed. When coupled with early weaning caused psychological, environmental and nutritional stress, a series of problems of early weaned piglets appear including reduction of immune function and diarrhea, some even lead to death, which affect the economic benefits of farmers and companies.

At present, the piglet fodder additives market is uneven in quality, some of them cause economic losses to companies and farmers. Many farmers were promoted by advertisements of the manufactures to add additives no matter whether they are needed, regardless of livestock and poultry varieties and physiological period. They even believe that the more varieties used, the better effect they will get, which results not only the missing of the expected effect, but also reduction of the production, or even poisoning and diseases. Even worse, long term abuse of drugs and growth promoter, in particular antibacterial drugs, would result in appearance of drug-resistant pathogenic bacteria in livestock and poultry products, which directly endanger human health. In recent years, some meat products have been re-treated from the international market, due to the addition of some additives in the fodder that does not meet the requirements, resulting in serious economic losses and impact. In addition, under the situation that there are enough supply in the market, people are concerned about the quality of food. Thus, pollution-free "green" livestock and poultry products are desired. To produce "green" livestock and poultry products, we must use the green fodder additives.

Therefore, the development of new fodder additives is critical to improve the immunity and the disease resistance of weaned piglets, control the mortality rate of weaned piglets, and provide a more balanced nutrition to weaned piglets.

CONTENT OF THE INVENTION

An object of the present invention is to provide a formulation of complex carbohydrates for fodder and fodder containing the said formulation. The aim of the present invention is to provide fodder with the formulation of complex carbohydrates which has a comprehensive and balanced nutrition to meet the nutritional requirement of weaned piglets. The fodder should also be able to enhance immunity and improve the disease resistance of weaned piglets. Moreover, the product should have good palatability, can improve the daily fodder intake, enhance average daily gain, decrease the ratio of fodder and meat, and reduce the incidence of diarrhea in piglets.

In order to achieve the above purpose, the invention provides the following technical solution:

A formulation of complex carbohydrates for fodder, comprising of 10-15% fucose, 5-20% galactose, 5-10% N-acetylgalactosamine, 10-30% glucosamine, 5-20% N-acetylglucosamine, 5-10% glucuronic acid, 10-15% mannose, 5-20% sialic acid and 10-15% xylose by weight percentage.

Preferably, the formulation of complex carbohydrates consists of 10% fucose, 5% galactose, 5% N-acetylgalactosamine, 30% glucosamine, 20% N-acetylglucosamine, 5% glucuronic acid, 10% mannose, 5% sialic acid and 10% xylose by weight percentage.

Or, the formulation of complex carbohydrates consists of 15% fucose, 20% galactose, 10% N-acetylgalactosamine, 10% glucosamine, 5% N-acetylglucosamine, 10% glucuronic acid, 15% mannose, 5% sialic acid and 10% xylose by weight percentage.

Or, the formulation of complex carbohydrates composed of 10% fucose, 5% galactose, 5% N-acetylgalactosamine, 10% glucosamine, 20% N-acetylglucosamine, 5% glucuronic acid, 10% mannose, 20% sialic acid and 15% xylose by weight percentage.

A fodder for weaned piglets, which includes 0.05-0.5 of the above mentioned formulation of complex carbohydrates in weight portion.

Further, said fodder further comprises the following raw materials in weight portion: corn 60-65, bean pulp 15-20, whey powder 3-6, fish flour 2-5, soybean protein concentrate 2-5, wheat short 2-5, piglets premix 4, glucose 2-3.

Piglet premix, which is purchased from the market, may contain calcium hydrogen ephosphate, mineral meal, lysine, methionine, vitamins and trace elements.

Unless specially indicated, the ingredients of the present invention are the normal products sold on the market for weaned piglets.

In the present invention, the fodder for weaned piglets is prepared using following method: crushing the corn and bean pulp while other raw materials remain uncrushed, then weighed separately and mix through mixer.

Another aspect of the present invention is the use of the fodder in improving the immunity of weaned piglets, enhancing the daily gain and reducing the incidence of diarrhea in weaned piglets.

The nine different monosaccharides used in the present invention are involved in the modification of protein and fat, as well as manipulating biochemical reactions. Moreover, each of them also has their particular biological activity, for example:

Fucose has functions of promoting embryo implantation and nerve conduction, immune regulation, inhibiting cancer and metastasis, reducing respiratory tract infection and regulating the activity of collagen.

Galactose is a component of lactose in the milk of mammals. It is often found in the form of D-galactose in nature, and exist in the brain and nerve tissue. It is also an important component of certain glycoproteins.

N-acetylgalactosamine is essential for the signal transduction between cells, and enriched in the sensory nerve of animals.

Glucosamine and N-acetylglucosamine is used as a therapeutic agent for osteoarthritis and rheumatoid arthritis.

Glucuronic acid plays an important role in animal metabolism. In animal body, it interacts with phenols, aromatic carboxylic acids and sterols, to form glucuronic acid esters, which can be excreted from the animal body. Therefore, the glucuronic acid has detoxification function in the animal. In addition, glucuronolactone is used as hepatoprotective drug and food poisoning antidote.

Mannose regulates immune system, increases wound healing, has anti-inflammation function, inhibits tumor growth and metastasis, increases the survival rate of cancer patients and inhibits certain bacterial infections, such as urinary tract infections.

Sialic acid is involved in preventing the invasion of bacteria. It is the receptor of influenza virus. Influenza virus recognize and interact with sialic acid to bind to the mucus cells. Adequate supply of sialic acid is particularly important for the development of the brain function of infants with low birth weight. The sialic acid in breast milk is also very important for ensuring the development of infants. Moreover, the content of the sialic acid also had a significant correlation with the content of DHA. This correlation also indicates that sialic acid is related to brain structure and brain function development of infants.

Xylose has the function of helping the growth of probiotic bacteria while inhibiting growth of pathogens, especially gram negative pathogenic bacteria and the fungal pathogen *Candida albicans*.

The formulation of complex carbohydrates and fodder containing the same of the present invention contains nine monosaccharide components essential for living. With scientific compatibility, it can meet the needs of different physiological stages of the organism, relieve the influence of weaning stress, improve the health status, and promote the level of pig production.

DETAILED DESCRIPTION AND EMBODIMENTS

The present invention can be in more detail using following embodiments.

EXAMPLE 1

A formulation of complex carbohydrates for fodder, which composed of 10% fucose, 5% galactose, 5% N-acetylgalactosamine, 30% glucosamine, 20% N-acetylglucosamine and 5% glucuronic acid, 10% mannose, 5% sialic acid and 10% xylose by weight percentage.

EXAMPLE 2

A formulation of complex carbohydrates for fodder, which composed of 15% fucose, 20% galactose, 10% N-acetylgalactosamine, 10% glucosamine, 5% N-acetylglucosamine and 10% glucuronic acid, 15% mannose, 5% sialic acid and 10% xylose by weight percentage.

EXAMPLE 3

A formulation of complex carbohydrates for fodder, which composed of 10% fucose, 5% galactose, 5% N-acetylgalactosamine, 10% glucosamine, 20% N-acetylglucosamine and 5% glucuronic acid, 10% mannose, 20% sialic acid and 15% xylose by weight percentage.

EXAMPLE 4

One kind of fodder for weaned piglets, which comprises the following raw materials in weight portion: corn 60, bean pulp 15, whey powder 3, fish flour 2, soybean protein concentrate 2, wheat short 2, piglets premix 4, glucose 2 and 0.05 of the mentioned formulation of complex carbohydrates in example 1.

EXAMPLE 5

One kind of fodder for weaned piglets, which comprises the following raw materials in weight portion: corn 60, bean pulp 20, whey powder 6, fish flour 5, soybean protein concentrate 5, wheat short 5, piglets premix 4, glucose 3 and 0.5 of the mentioned formulation of complex carbohydrates in example 2.

EXAMPLE 6

One kind of fodder for weaned piglets, which comprises the following raw materials in weight portion: corn 60, bean pulp 20, whey powder 6, fish flour 5, soybean protein concentrate 5, wheat short 5, piglets premix 4, glucose 3 and 0.5 of the mentioned formulation of complex carbohydrates in example 3.

In order to further illustrate the effect of the present invention, the following experiments are conducted:

1. Experimental Animals and Groups

Using the single factor experiment design, 240 of 28 day old weaned and healthy Duroc*Landrace*Yorkshire crossbred piglets were selected and randomly divided into 4 treatments, each treatment divided into 6 replicates with 10 piglets per replicate. The control group of piglets were fed with the basal diet; the test group of piglets #1 with the basal diet and 0.05 weight portions of the formulation of complex carbohydrates in example 1; the test group of piglets #2 with the basal diet and 0.2 weight portions of the formulation of complex carbohydrates in example 2. the test group of piglets #3 with the basal diet and 0.5 weight portions of the formulation of complex carbohydrates in example 3. The experimental period was 4 weeks.

According to NRC (1998), the formula of the basic diet of piglets was formulated (in weight): corn 60.08, bean pulp 20, whey powder 5, fish flour 4, and soybean protein concentrate 2.5, wheat short 2.5, glucose 2.2 and piglets premix 4.

2. Specific Test Procedure

Experiments were carried out in a commercial farm with at least 10,000 pigs, feeding and management procedures according to the provisions of the experimental farm. The weight of piglets was weighed according to the weight of piglets with an empty stomach in the morning of the beginning (D0) and end (D28) of the experiment. The health of piglets was observed during the whole experiment, while the incidence of morbidity, mortality, diarrhea and defective rate recorded. Feed tanks were cleaned and piglets hungered for 12 hours in the end of the experiment. One healthy piglet was chosen from each replicate, blood sampled form jugular vein and stored in the refrigerator for further test.

3. Measurement Indexes

The average daily weight gain (ADG), average daily feed intake (ADFI) and ratio of feed to meat (F/G), mortality and diarrhea rate of piglets were measured. Levels of IL-2, IL-10 and IFN-γ were measured by ELISA kit, and the operation was performed in strict accordance with instructions.

4. Statistical Analysis

SAS statistical software was used for variance analysis, and Duncan's multiple comparison was used.

1) The effects of different formulation of complex carbohydrates on the performance of piglets were shown in Table 1:

TABLE 1

Effect of formulation of complex carbohydrates on growth performance of piglets

|  | NC | Group 1 | Group 2 | Group 3 |
|---|---|---|---|---|
| $D_0$ (kg) | 8.72 | 8.66 | 8.78 | 8.70 |
| $D_{28}$ (kg) | 21.58 | 22.22 | 23.88 | 24.10 |
| ADG (g) | 459 | 484 | 539 | 550 |
| ADFI (g) | 807 | 826 | 927 | 952 |
| F/G (g/g) | 1.76 | 1.70 | 1.71 | 1.73 |

As shown in Table 1, the average daily gain (ADG) of weaned piglets was significantly improved, and the daily feed intake (ADFI) and the ratio of feed to meat (F/G) were improved.

2) The effects of different formulation of complex carbohydrates on the levels of IL-2, IL-10 and IFN-γ in the serum of piglets are shown in Table 2:

TABLE 2

Effect of formulation of complex carbohydrates on serum cytokines of piglets

|  | NC | Group 1 | Group 2 | Group 3 |
|---|---|---|---|---|
| IFN-γ | 62.62 | 73.12 | 84.04 | 88.12 |
| IL-2 | 103.98 | 117.53 | 124.89 | 127.53 |
| IL-10 | 110.75 | 115.34 | 119.86 | 124.62 |

Table 2 shows that the addition of formulation of complex carbohydrates can increase the level of IL-10, IL-2 and IFN-in serum, enhance the immune function of weaned piglets, and improve their resistance to disease.

3) The effect of different formulations of complex carbohydrates on the diarrhea rate of piglets are shown in Table 3:

TABLE 3

Effect of formulation of complex carbohydrates on diarrhea rate of piglets

|  | NC | Group 1 | Group 2 | Group 3 |
|---|---|---|---|---|
| Diarrhea (%) | 14.3 | 7.2 | 6.5 | 5.9 |

As shown in Table 3, adding formulation of complex carbohydrates of the present invention to the diet can reduce the diarrhea rate of piglets.

In conclusion, the addition of the formulation of complex carbohydrates in the diet can improve the growth performance of piglets, and 500 mg/kg is the concentration shows the most significant effect. The formulation of complex carbohydrates can improve the content of serum cytokines in piglets, enhance their immunity, and reduce the diarrhea rate of piglets.

The safety experiment of the fodder formula described in the present invention is as follows:

Materials and methods: nine 28-day old healthy weaned Duroc*Landrace*Yorkshire hybrid piglets were fed with fodder containing formulation of complex carbohydrates. The experimental period was 30 days, during which the manifestations of poisoning and death were observed.

The fodder contains the following components: corn 62.5 g, bean pulp 15 g, whey powder 2 g, fish flour 2 g, soybean protein concentrate 5 g, wheat short 2 g, piglets premix 3 g, glucose 4 g and 0.5 g of formulation of complex carbohydrates.

Results: after feeding the piglets with the above experimental diets for 30 days, no poisoning, death or obvious abnormalities in the main organs were observed.

Conclusion: add 0.5% weight percent of formulation of complex carbohydrates in the diet is safe for piglets.

In conclusion, the experiment result of the weaned piglets with the compound fodder of the invention showed that:

After feeding the above mentioned fodder for 4 weeks, the ADFI, ADG and F/G was 799-900 g, 350-550 g and 1.7-1.8 respectively.

After feeding the above mentioned fodder for 4 weeks, the morbidity, mortality, diarrhea and defective rate was significantly reduced.

After feeding the above mentioned fodder for 4 weeks, the level of IL-10, IL-2 and IFN-in serum increased, and the immune function of weaned piglets was also effectively enhanced.

What is claimed is:

1. A formulation of complex carbohydrates for fodder, comprising 10-15% fucose, 5-20% galactose, 5-10% N-acetylgalactosamine, 10-30% glucosamine, 5-20% N-acetylglucosamine and 5-10% glucuronic acid, 10-15% mannose, 5-20% sialic acid and 10-15% xylose by weight percentage.

2. The formulation of complex carbohydrates for fodder according to claim 1, wherein the formulation consists of 10% fucose, 5% galactose, 5% N-acetylgalactosamine, 30% glucosamine, 20% N-acetylglucosamine and 5% glucuronic acid, 10% mannose, 5% sialic acid and 10% xylose by weight percentage.

3. The formulation of complex carbohydrates for fodder according to claim 1, wherein the formulation consists of 15% fucose, 20% galactose, 10% N-acetylgalactosamine, 10% glucosamine, 5% N-acetylglucosamine and 10% glucuronic acid, 15% mannose, 5% sialic acid and 10% xylose by weight percentage.

4. The formulation of complex carbohydrates for fodder according to claim 1, wherein the formulation consists of 10% fucose, 5% galactose, 5% N-acetylgalactosamine, 10% glucosamine, 20% N-acetylglucosamine and 5% glucuronic acid, 10% mannose, 20% sialic acid and 15% xylose by weight percentage.

5. A fodder for weaned piglets, wherein the fodder comprises 0.05-0.5% of the formulation of complex carbohydrates of claim 1 by weight.

6. The fodder of claim 5, wherein the fodder comprises the following raw materials in weight portion: corn 60-65, bean pulp 15-20, whey powder 3-6, fish flour 2-5, soybean protein concentrate 2-5, wheat short 2-5, piglets premix 4, glucose 2-3.

7. A method of enhancing the immunity of weaned piglets, comprising feeding the fodder according to claim 5 to the weaned piglets.

8. A method of increasing daily weight gain of weaned piglets, comprising feeding the fodder according to claim 5 to the weaned piglets.

9. A method of reducing incidence of diarrhea in weaned piglets, comprising feeding the fodder according to claim 5 to the weaned piglets.

* * * * *